US011352615B2

(12) United States Patent
Altrogge et al.

(10) Patent No.: US 11,352,615 B2
(45) Date of Patent: *Jun. 7, 2022

(54) DEVICE AND METHOD FOR LARGE VOLUME TRANSFECTION

(71) Applicant: Lonza Cologne GmbH, Cologne (DE)

(72) Inventors: Ludger Altrogge, Metternich (DE); Timo Gleissner, Euskirchen (DE); Andreas Heinze, Cologne (DE); Sven Hermsmeier, Bonn (DE)

(73) Assignee: Lonza Cologne GmbH, Cologne (DE)

( * ) Notice: Subject to any disclaimer, the term of this patent is extended or adjusted under 35 U.S.C. 154(b) by 140 days.

This patent is subject to a terminal disclaimer.

(21) Appl. No.: 16/185,045

(22) Filed: Nov. 9, 2018

(65) Prior Publication Data
US 2019/0144844 A1 May 16, 2019

Related U.S. Application Data

(63) Continuation of application No. 15/308,363, filed as application No. PCT/EP2015/059150 on Apr. 28, 2015, now Pat. No. 10,336,996.

(30) Foreign Application Priority Data

May 2, 2014 (EP) .................................... 14166918

(51) Int. Cl.
*C12N 13/00* (2006.01)
*C12M 3/00* (2006.01)
(Continued)

(52) U.S. Cl.
CPC ........... *C12N 13/00* (2013.01); *A61N 1/0412* (2013.01); *C12M 35/02* (2013.01); *C12N 15/87* (2013.01)

(58) Field of Classification Search
CPC ...... C12M 35/00; C12M 35/02; C12M 41/30; B01L 3/5027; B01L 3/502715
See application file for complete search history.

(56) References Cited

U.S. PATENT DOCUMENTS 3,148,624 A    9/1964  Baldwin
5,183,744 A *  2/1993  Kawamura ............ C12M 35/02
                                                     435/2
(Continued)

FOREIGN PATENT DOCUMENTS

DE         10127247        12/2006
JP         2008509653 A     4/2008
(Continued)

OTHER PUBLICATIONS

S.M. Kennedy et al.: "Quantification of Electroporative Uptake Kinetics and Electric Field Heterogeneity Effects in Cells", Biophysical Journal, vol. 94, No. 12, Jun. 1, 2008, pp. 5018-5027, XP055166631.
(Continued)

*Primary Examiner* — Nathan A Bowers
(74) *Attorney, Agent, or Firm* — Agris & Von Natzmer, LLP; Joyce von Natzmer

(57) ABSTRACT

The invention relates to a device (1) for applying an electric field to a suspension of cells, cell derivatives, organelles, sub-cellular particles and/or vesicles, comprising at least one chamber (6) which comprises at least two electrodes (4), and at least one separating element (13) which is movable within the chamber (6) between two terminal points (14, 15) and, if it is in a position between the terminal points (14, 15), separates at least one first compartment (26) of the chamber (6) from at least one second compartment (27) of the chamber (6). According to the invention each compartment (26, 27) is designed to hold the suspension and comprises at least one port (7, 8, 10, 11) for charging or discharging the
(Continued)

suspension, so as to discharge an aliquot of the suspension from the chamber (6) and at the same time charge a further aliquot of the suspension into the chamber (6), wherein the separating element (13) is moved in a second direction opposite to a first direction, and wherein the separating element (13) separates the aliquots from each other.

13 Claims, 9 Drawing Sheets

(51) Int. Cl.
  *C12M 1/42* (2006.01)
  *C12N 15/87* (2006.01)
  *A61N 1/04* (2006.01)

(56) References Cited

U.S. PATENT DOCUMENTS

| | | | |
|---|---|---|---|
| 5,563,067 A * | 10/1996 | Sugihara | C12M 41/46 |
| | | | 435/287.1 |
| 6,150,148 A | 11/2000 | Nanda et al. | |
| 6,773,669 B1 | 8/2004 | Holaday et al. | |
| 7,771,984 B2 | 8/2010 | Dzekunov et al. | |
| 2003/0073238 A1 | 4/2003 | Dzekunov et al. | |
| 2004/0180426 A1 * | 9/2004 | Maher | G01N 33/5008 |
| | | | 435/287.2 |
| 2007/0128708 A1 | 6/2007 | Gamelin | |
| 2008/0213855 A1 | 9/2008 | Firth et al. | |
| 2009/0053813 A1 * | 2/2009 | Evans | C12N 13/00 |
| | | | 435/461 |
| 2012/0087841 A1 * | 4/2012 | Altrogge | C12M 23/12 |
| | | | 422/186.04 |
| 2012/0107181 A1 | 5/2012 | Cedillo et al. | |
| 2013/0089931 A1 * | 4/2013 | Joo | C12N 15/02 |
| | | | 435/450 |
| 2013/0260434 A1 | 10/2013 | Mueller-Hartmann et al. | |

FOREIGN PATENT DOCUMENTS

| | | |
|---|---|---|
| JP | 6384481 B2 | 9/2018 |
| WO | 2005113820 A2 | 12/2005 |
| WO | 2004083379 A3 | 3/2006 |
| WO | 2007120234 A2 | 10/2007 |
| WO | 2008133655 A2 | 11/2008 |
| WO | 2011161092 A1 | 12/2011 |
| WO | 2015165881 A1 | 11/2015 |

OTHER PUBLICATIONS

Japanese Patent Office, Office Action issued in appl. no. 2016-564620 dated Feb. 26, 2019 (Original and English translation).
Australian Patent Office: Examination Report for AU 2018205130 dated Jun. 29, 2019.
Australian Patent Office: Claims as accepted for AU 2018205130 dated Mar. 2, 2020 prior to notice of grant dated Jun. 25, 2020 as retrieved from: http://pericles.ipaustralia.gov.au/ols/auspat/applicationDetails.do?applicationNo=2018205130 (Mar. 2, 2020, retrieved on Feb. 1, 2022).

* cited by examiner

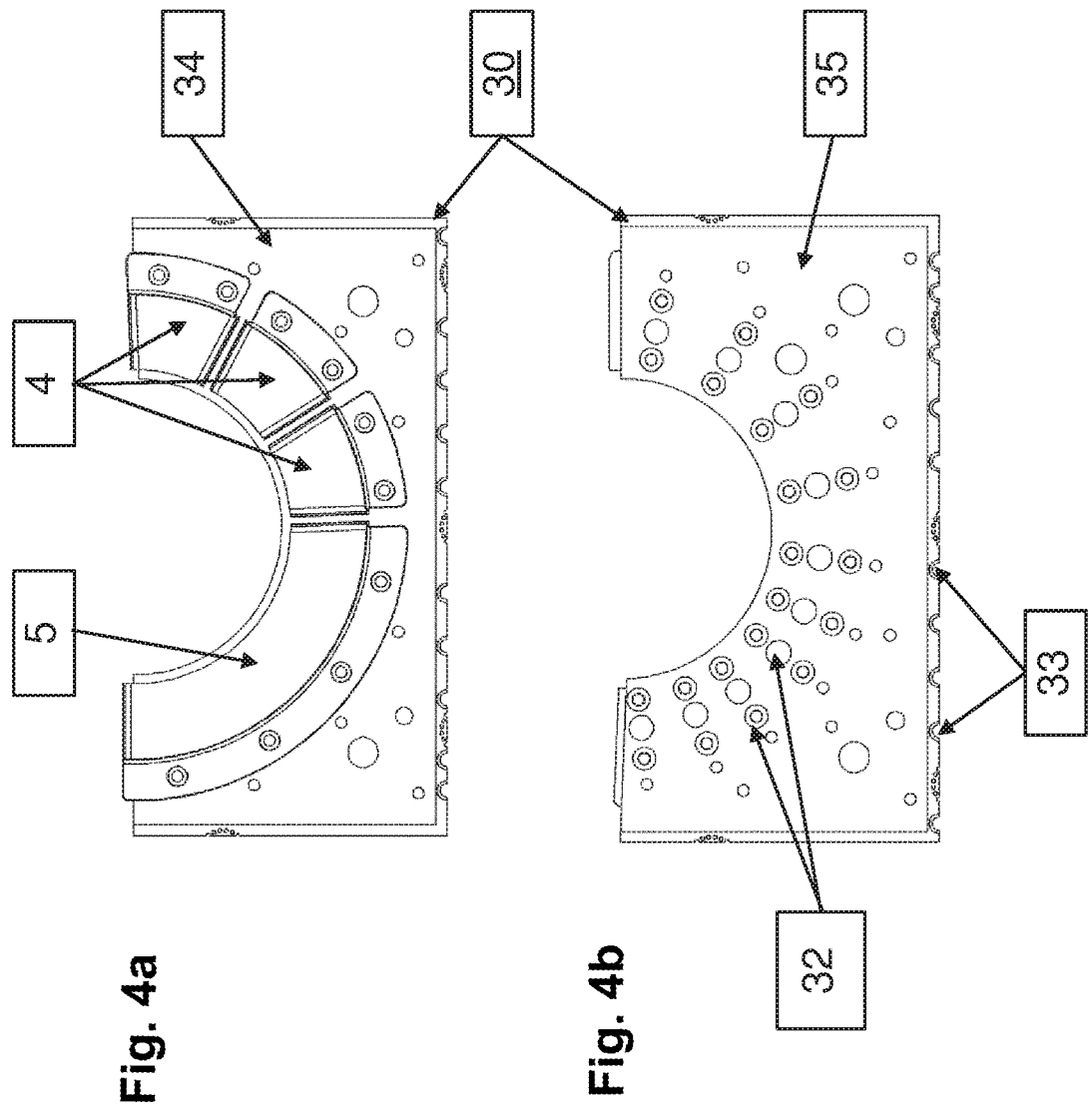

DEVICE AND METHOD FOR LARGE VOLUME TRANSFECTION

CROSS-REFERENCE TO RELATED APPLICATIONS

This is a continuation application of U.S. patent application Ser. No. 15/308,363, which is the U.S. national stage of International application PCT/EP2015/059150, filed Apr. 28, 2015 designating the United States, claiming priority to European application EP 14166918.4, filed May 2, 2014.

FIELD OF THE INVENTION

The invention relates to a device for applying an electric field to a suspension of cells, cell derivatives, organelles, sub-cellular particles and/or vesicles, comprising at least one chamber which comprises at least two electrodes and at least one separating element which is movable within the chamber between two terminal points and, if it is in a position between the terminal points, separates at least one first compartment of the chamber from at least one second compartment of the chamber. The invention further concerns a method for applying an electric field to a suspension of cells, cell derivatives, organelles, sub-cellular particles and/or vesicles.

BACKGROUND OF AND INTRODUCTION TO THE INVENTION

The introduction of biologically active molecules, for example DNA, RNA or proteins, into living cells, cell derivatives, organelles, sub-cellular particles and/or vesicles may, e.g., serve to examine the biological functions of these molecules and is, moreover, an essential precondition for the success of the therapeutic use of these molecules, e.g., in gene therapy. A preferred method for introducing external molecules into the cells is called electroporation, which unlike chemical methods limits undesirable changes in the structure and function of the target cell. In electroporation the external molecules are introduced into the cells from an aqueous solution, preferably a buffer solution specifically adapted to the cells, or a cell culture medium, via a short current flow, i.e., e.g., the pulse of a discharging capacitor which renders the cell membrane transiently permeable to the external molecules. The temporary "pores" that are formed in the cell membrane allow the biologically active molecules to first reach the cytoplasm in which they may already perform their function or exert any therapeutic action to be examined, and then, under certain conditions, to also reach the cell nucleus as it is required, e.g., in gene therapy applications.

Due to a short application of a strong electrical field, i.e. a short pulse with a high current density, cells, cell derivatives, organelles, sub-cellular particles and/or vesicles may also be fused. In this so-called electrofusion the cells are, e.g., initially brought into close membrane contact by an inhomogeneous electrical alternating field. The subsequent application of an electrical field pulse leads to interaction between membrane parts, which ultimately results in fusion. Devices comparable to those used for electroporation may be used for electrofusion as well.

Smaller volumes of suspension of cells, cell derivatives, organelles, sub-cellular particles and/or vesicles are generally treated in a batch process in relatively simple vessels. The solution or cell suspension, respectively, is frequently located in a cuvette, i.e. a narrow vessel open at the top, which in the vicinity of the bottom has two opposing, parallel electrodes in the lateral walls which serve to apply the electrical voltage. However, such vessels are unsuitable for treating larger volumes as the reaction space available for the electrical treatment is limited by the limited maximal distance between the electrodes. Thus, flow-through processes in which the cell or vesicle suspension is continuously or discontinuously fed through the reaction space between the electrodes are often used for the electroporation or electrofusion of larger volumes.

U.S. Pat. No. 6,150,148, for example, discloses a cuvette modified for flow-through processes. The port of the cuvette is sealed by a cap through which a feed line is guided. At the bottom in a region between the electrodes the cuvette has an additional port to which a discharge is connected. Because of this arrangement the suspension to be treated can be fed through the feed line into the reaction space and exit it through the discharge. Due to repeated, continuous or discontinuous exchange of the suspension in the reaction room and the respective repeated electrical pulsing, larger volumes can be treated with this cuvette. U.S. Pat. No. 6,150,148 further discloses flow-through chambers which are of tubular or slotted design and at their ends each have a connection for an input and an output channel. The chambers themselves represent an oblong reaction space which is enclosed by two cylindrical, concentrically arranged or flat electrodes having plane-parallel configuration. These devices also allow larger volumes to be treated by repetitive pulsing as they are fed through the chamber.

However, those flow-through electroporation or even electrofusion processes are difficult to control as the flow-through velocity has to be brought in line with the frequency of pulsing. Heating of the suspension and formation of gas bubbles by electrolysis pose further significant problems. Repetitive generation of the very high currents often required for these processes leads to increased heat production and large numbers of small gas bubbles that are formed by electrochemical processes in the electrolyte solution in which the cells or vesicles to be treated are suspended. These bubbles disturb the flow of the suspension through the chamber and may result in a backflow of the suspension already treated into the chamber. Moreover, the risk of arcing is increased as the suspension is unevenly distributed within the chamber. These problems, on the one hand, lead to results that are no longer reproducible and on the other hand, if living cells are treated, to an increased mortality rate.

WO 2004/083379 A2 discloses an electroporation method for insertion of exogenous material into vesicles with which the treatment volume of the suspension is scalable and the time of treatment of the vesicles in the chamber is substantially uniform. In this method, the suspension volume is greater than the volume of the chamber of the electroporation device. An initial portion of the suspension volume is moved into the chamber, retained and treated in the chamber, and moved out from the chamber. An additional portion of the suspension volume is then moved into the chamber, retained and treated in the chamber, and moved out from the chamber. Further portions of the suspension volume are sequentially moved into the chamber, retained and treated in the chamber, and moved out from the chamber until the suspension volume is depleted.

WO 2005/113820 A2 discloses an electroporation device comprising a regulated flow electroporation chamber that enables conditions in which a sample is uniformly processed in individual fractions or volumes in a fully closed sterile system. The chamber includes an inlet port and an outlet port, through which the cell suspension to be processed can be loaded into and displaced from the chamber, respectively, so that samples of the suspension can be processed in units which are produced by providing a boundary between unprocessed and processed volumes of the sample. The boundary is provided by cycling a non-sample gas or fluid into the chamber between two fractions of the sample. The non-sample gas or fluid may flow in or out of the chamber through a third port of the chamber.

US 2007/0128708 A1 discloses a scalable device for electroporating relatively large volumes of a fluid medium carrying biological cells or vesicles in a segmented chamber, wherein each segment comprises two electrodes. The effective volume of the chamber can be varied by moving a plunger along the longitudinal axis of the chamber. Thus, the volume chosen is directly related to the volume of the sample to be electroporated. The sample is sucked in and purged out of the chamber through a port disposed in the end wall of the chamber. The sample within the chamber is processed by sequentially applying voltage pulses to the electrode pairs of the individual segments of the chamber.

However, it is a drawback of the prior art devices and methods that the processing of larger volumes is time-consuming since a sample already processed has to be completely discharged from the chamber before the next sample can be charged into the chamber. It is another drawback of the prior art devices and methods that bubbles and cell debris are not completely removed from the reaction chamber in a reliable manner.

It is therefore an object of the invention to provide a device and a method for treating cells, cell derivatives, organelles, sub-cellular particles and/or vesicles, with which the processing of larger volumes is accelerated, which enable treatment under reproducible conditions, and which ensure reliable clearing of the reaction chamber after the treatment.

SUMMARY OF THE INVENTION

The object is met by a device for applying an electric field to a suspension of cells, cell derivatives, organelles, sub-cellular particles and/or vesicles as initially specified, with which each compartment of the chamber is designed to hold the suspension and comprises at least one port for charging or discharging the suspension. That is, each compartment of the chamber can receive and hold an aliquot of the suspension which is movable in and out of the chamber through at least two ports, wherein each compartment is provided with at least one port through which the respective compartment can be filled with the suspension and/or through which the suspension can be purged out of this compartment. This advantageous configuration allows for simultaneous charging and discharging of the chamber so that the time necessary for changing the suspension and hence the time lag between two subsequent electrical treatments of the suspension is minimized. This minimization results in a significant acceleration of the processing time for large volumes, i.e. volumes above 1 ml. It is another advantage of the device according to the invention that it enables a scalable process by repetitive charging and processing of the suspension. For example, if the chamber has a total volume of 1 ml, any multiple volume thereof can be easily processed in an expedited manner.

Accordingly, the device according to the invention is not a flow-through device but a device that enables charging and discharging of the chamber at the same time by a kind of push-pull mechanism.

According to an exemplary embodiment of the invention at least one port is disposed at one end of the chamber and at least one further port is disposed at the opposite end of the chamber. Provision of the ports at opposite ends of the chamber allows for easily establishing the push-pull mechanism where the separating element, and thus the suspension, can be moved between two terminal points of the chamber so as to simultaneously charge one compartment at one end of the chamber and discharge another compartment at the opposite end of the chamber. Moreover, such geometric arrangement allows for optimal integration of the device according to the invention in an electroporation or electrofusion system as the ports are separated from each other and thus can be accessed from different ends of the device.

In an embodiment where at least two ports are disposed at each end of the chamber, one port may be used as an inlet port for charging the suspension while the other port may be used as an outlet port for discharging the suspension.

Minimization of dead volumes can be achieved by reducing the size of the chamber port(s), in particular the inlet port(s). An additional or alternative measure for ensuring small dead volumes can be the use of Y-connections of tubes close to the chamber outlet/inlet ports.

Moreover, attaching tubes to the outlet ports of the device allows for pressure peak compensation in the chamber.

In another embodiment of the invention the separating element is coupled to at least one adjusting element which operates and/or controls the separating element. In an advantageous embodiment the adjusting element is disposed outside the chamber so that each compartment is devoid of any interfering element that might affect the function of the device according to the invention. For example, the separating element may be moved within the chamber at least partially by means of the adjusting element.

The adjusting element can be, e.g., a rotatable body which is operatively coupled with the separating element. For example, the rotatable body may be a rotor-like element that moves the separating element such that it performs a rotational movement. Such embodiments ensure precise control and constant movement of the separating element, in particular if the chamber has a curved shape. However, in an alternative embodiment of the invention, the adjusting element and hence the separating element may perform a movement in another direction, e.g., in a linear direction.

The separating element may be driven by the adjusting element via a component selected from the group consisting of a worm gear, a spur gear, a bevel gear, a gear rod, a belt drive, and a square-bar steel. However, other gear mechanisms or power transmission elements can be used as well, if suitable.

According to another exemplary embodiment of the invention the separating element is a sealing member which ensures liquidproof and/or gasproof separation of the different compartments of the chamber if it is in a position between the terminal points. For example, the separating element can comprise a flexible and/or elastic material. Due to its elastic deformability, the separating element is further capable of compensating pressure peaks within the chamber. The separating element can be designed, e.g., as 2-component plastic part including an elastic material for better sealing properties. The separating element may further comprise sealing lips for optimal clearing of the chamber. To this end, the sealing lips can be oriented in a direction adapted to the inner surface of the chamber and/or the surface of the electrodes and/or the other components of the separating element. In an advantageous embodiment of the invention a potential deflection of the separating element or parts thereof can be limited by bump stops, so as to maintain its sealing function.

In one particular embodiment the separating element comprises at least two spaced parts, wherein the inner space between the spaced parts of the separating element comprises a compressible material. Such design provides effective pressure compensation so that the separating element acts as a kind of cushion that balances pressure variations in the chamber. The compressible material may simply be air or any other gas, or a compressible foam or cellular material.

According to another exemplary embodiment of the invention the chamber comprises at least two segments, wherein each segment comprises at least one electrode. It is an advantage of this embodiment that each segment can be electrically addressed individually so that controlled generation of electric fields within the chamber can be precisely achieved. For example, in order to avoid arcing and/or undesired heating of the suspension, voltage pulses can be applied to different segments of a compartment sequentially. To this end, each segment can be provided with at least one first electrode and at least one second electrode, wherein the second electrode may be a common electrode of at least two segments. In one embodiment of the invention each compartment of the chamber may comprise at least one segment being provided with at least one electrode.

The chamber of the device according to the invention comprises corresponding recesses of two components which are attached to each other. That is, the device according to the invention can be assembled, e.g., by attaching two components to each other, wherein each component comprises a recess that corresponds to the recess of the other component. If these two components are attached to each other, their aligned recesses form the chamber of the device. In order to be capable of producing an electric field within the chamber, each recess can be provided with at least one electrode. At least some of the electrodes may be segmented. For example, one half of the electrodes (at one side of the symmetry axis) can be segmented while the other half of the electrodes (at the other side of the symmetry axis) can be a single, unsegmented electrode which may be used as a counter electrode. In an advantageous embodiment the two components are identical so that cost-effective production is ensured. As the identical components are rotationally symmetric, easy assembly by attaching the components to each other is still possible in this case.

In one particular embodiment the chamber further comprises at least one base member which is at least substantially made of an insulating material and includes at least one surface to which the electrode is attached, wherein said surface comprises at least one conductive area designed to provide an electrical connection between the electrode and at least one electric contact point. The conductive area may be, e.g., at least one hole, a three dimensional feature of the surface, or a flat area. The hole can be a bore in the base member which is provided with an electrically conductive material, at least at its inner surface. The hole may be at least partially filled with an electrically conductive material providing an electrically conductive path from the electrode to the same or another surface of the base member. The three dimensional feature may be selected from the group consisting of pits, bumps, lines, recesses, depressions, protrusions and wells. The conductive area may be electrically coupled with at least one electric contact point via at least one conductive path, e.g., a Printed Circuit Board (PCB) track. The electric contact point is made of an electrically conductive material and designed to be contacted by at least one electric contact, e.g., a spring contact, providing direct or indirect electric connection to a power source. Using such base members allows for cost-effective production of the device according to the invention since members including electrodes and corresponding contact points can be produced in a time-saving one-step manufacturing process. Moreover, in this embodiment electrode design is independent of the location of the electrical contacts so that optimized electrode design can be combined with an optimal electrical connection. The means for contacting the electrodes can be designed independently of electrode design and position.

In an advantageous embodiment of the invention the base member can be a Printed Circuit Board (PCB) or the like. The PCB may include an internal thermistor (thermal resistor) for better temperature control, so as to allow for slowing down processing of the suspension in order to allow heat dissipation.

For example, the electrodes can be made of an electrically conductive polymer, in particular a polymer doped with electrically conductive material. The polymer may consist of or be at least based on polycarbonate, polyetheretherketone, polypropylene, polyamide, polyphenylensulfide or a mixture of these polymers. The polymer can be doped with, e.g., carbon fibres, graphite, soot, carbon nanotubes and/or an intrinsically conductive synthetic material. Alternatively, an intrinsically conductive polymer, such as polyaniline, polyacetylene, poly-para-phenylene, poly-para-phenylensulfide, polypyrrole, polythiophene, polypropylene or the like, may be used as electrode material.

In order to provide a suitable base member, the polymer can be molded over one side of the base member provided with at least two conductive areas at one or more sides of the base member, wherein the polymer forms a close physical contact at least partially to at least one conductive area, wherein the conductive areas can be flat or the surface of a pit in or a hole through the base member and the polymer extends into the pits or through the holes and forms electrically conductive paths from the electrodes to contact points not overmolded with the conductive polymer.

It is one aspect of the invention to provide a device for applying an electric field to a suspension of cells, organelles and/or vesicles, comprising at least one chamber for holding the suspension, wherein the chamber comprises at least one electrode, and wherein the chamber further comprises at least one base member which is at least substantially made of an insulating material and includes a surface to which the electrode is attached, wherein said surface includes at least one conductive area designed to provide an electrical connection between the electrode and at least one electric contact point. The conductive area on the surface of the base member may be a pit or hole being at least partially overmolded or filled with an electrically conductive material and providing an electrically conductive path from the electrode to the contact point. With this device it may be beneficial if the electrode and the electrically conductive material are made of the same material. For example, the electrodes can be made of an electrically conductive polymer, in particular a polymer doped with electrically conductive material or an intrinsically conductive polymer as described above. The polymer can be molded over one side of the base member and can form a close physical contact to a flat conductive area, or extend into conductively plated pits or through conductively plated holes, so as to form electrically conductive paths from the electrode to the contact point. In an advantageous embodiment of the invention the base member can be a Printed Circuit Board (PCB) or the like.

Contacting of electrodes by overmolding of PCBs allows for designing the electrodes independently of the location of the electrical contacts so that optimized electrode design can be combined with an optimal electrical connection. That is, the means for contacting the electrodes can be designed independently of electrode design and position. The PCB may include an internal thermistor or any other temperature sensitive electrical component, for better temperature control, so as to allow for slowing down processing of the suspension to allow heat dissipation.

Alternatively, the electrodes of the chamber may be made of metal, e.g., aluminum, or any other conductive material.

The device according to the invention may further comprise means for fixing the separating element outside the chamber, so that the scalable chamber can be easily transformed into a static chamber having a fixed volume. For example, the static variant of the device may have a fixed processing volume of about 0.5 ml, 1.0 ml, 1.5 ml, or 2.0 ml.

In order to seal the chamber against other components of the device according to the invention, at least one gasket can be disposed between the adjusting element and the chamber.

The chamber may further comprise at least one sealing inlay which at least partially extends along one side of the chamber so as to seal this side against the environment. This sealing inlay may be disposed at one side of the chamber opposite to the gasket mentioned above, i.e. at the side of the chamber opposite to the adjusting element. If the sealing inlay comprises an elastic and compressible material, it additionally enables pressure compensation within the chamber. The sealing inlay can be made of silicone foam or a similar inert material.

According to another exemplary embodiment the device according to the invention may further comprise stacking means for attaching this device to another device according to the invention. That is, the performance of an electroporation or electrofusion system can be easily enhanced by stacking a plurality of devices according to the invention, so as to increase the volume processable per time unit. For example, the stacked devices may be coupled such that a plurality of chambers is connected in parallel. In this manner, it is advantageously possible to increase the total system volume, e.g., 10-fold.

Another approach to increase the capacity of the device according to the invention would be the provision of two or more chambers within one device. In this case, the chambers can be arranged in parallel or concentric.

With the stackable and/or multi-chamber version the total system volume can be easily increased up to 10 ml or even 100 ml or more. Basically, the number of cells, cell derivatives, organelles, sub-cellular particles and/or vesicles to be processed is not limited anyway. For example, a suitable scale-up enables processing of $10^7$ to $10^8$, $10^7$ to $10^9$ or $10^7$ to $10^{10}$ cells, cell derivatives, organelles, sub-cellular particles and/or vesicles.

In an advantageous embodiment of the invention the device is designed such that it has an upright orientation in the functional state. This upright orientation in combination with chamber outlet port(s) being disposed at the top of the chamber insures complete bubble removal.

The object is further met by a method for applying an electric field to a suspension of cells, cell derivatives, organelles, sub-cellular particles and/or vesicles, comprising:

a) Charging an aliquot of the suspension into at least one chamber of a device for applying an electric field to the suspension, said chamber comprising at least two electrodes, wherein a separating element disposed within the chamber is moved in a first direction;

b) Applying a voltage pulse to the aliquot via at least two electrodes of the chamber;

c) Discharging the aliquot from the chamber and at the same time charging a further aliquot of the suspension into the chamber, wherein the separating element is moved in a second direction opposite to the first direction, and wherein the separating element separates the aliquots from each other;

d) Applying a voltage pulse to the further aliquot via at least two electrodes of the chamber.

The process can be terminated at this point by completely discharging the further aliquot from the chamber, wherein the separating element is moved in the first direction opposite to the second direction.

In the advantageous method according to the invention simultaneous charging and discharging of the chamber is accomplished so that the time necessary for changing the suspension and hence the time lag between two subsequent electrical treatments of the suspension is minimized. This minimization results in a significant acceleration of the processing time for large volumes, i.e. volumes above 1 ml.

The method according to the invention can be continued for further processing of larger volumes by e) Discharging the further aliquot from the chamber and at the same time charging a further aliquot of the suspension into the chamber, wherein the separating element is moved in the first direction opposite to the second direction, and wherein the separating element separates the aliquots from each other;

f) Applying a voltage pulse to the further aliquot via at least two electrodes of the chamber;

g) Optionally, repeating steps c) to f) for further aliquots of the suspension until the whole suspension is processed.

Accordingly, due to repetitive charging and processing of the suspension, the method according to the invention is a scalable process. For example, if the chamber has a total volume of 1 ml, any multiple volume thereof can be easily processed in an expedited manner.

For example, the device used in said method can be the device according to the invention as described above.

For example, the separating element can be moved within the chamber at least partially by means of an adjusting element which is operatively coupled with the separating element. If the adjusting element is a rotatable body, e.g., a rotor-like element, the separating element may be moved by rotating the adjusting element. Such embodiment ensures precise control and constant movement of the separating element, in particular if the chamber has a curved shape. The suspension can be charged into and discharged from the chamber by means of a pumping element, e.g., a vacuum pump or a peristaltic pump or the like. To this end, the device according to the invention may be provided with Luer slip connectors, or any other connectors which are attachable and detachable, that render the device compatible with common pumping systems. The pumping pressure is supported by the movement of the separating element which wipes along the inner surfaces of the chamber so that complete displacement of the processed sample from the chamber is ensured. Moreover, the combination of pumping and wiping results in effective removal of air bubbles, cell debris, and any other particles.

In particular applications it might be necessary or advantageous to provide the cells, cell derivatives, organelles, sub-cellular particles and/or vesicles to be treated and the substrates or reactants in separate containments and mix them just prior to filling of the chamber and the subsequent treatment.

BRIEF DESCRIPTION OF THE FIGURES

The invention is further exemplarily described in detail with reference to the figures.

FIGS. 4a and 4b show different views of the base member according to FIG. 3, wherein FIG. 4a shows an inner side of the base member with electrodes; and FIG. 4b shows an outer side of the base member with conductive areas.

FIG. 5a shows an electrode extending through holes, FIG. 5b shows an electrode attached to a flat surface, and FIG. 5c shows an electrode attached to a recess.

DETAILED DESCRIPTION OF VARIOUS AND PREFERRED EMBODIMENTS

Figure 1A:
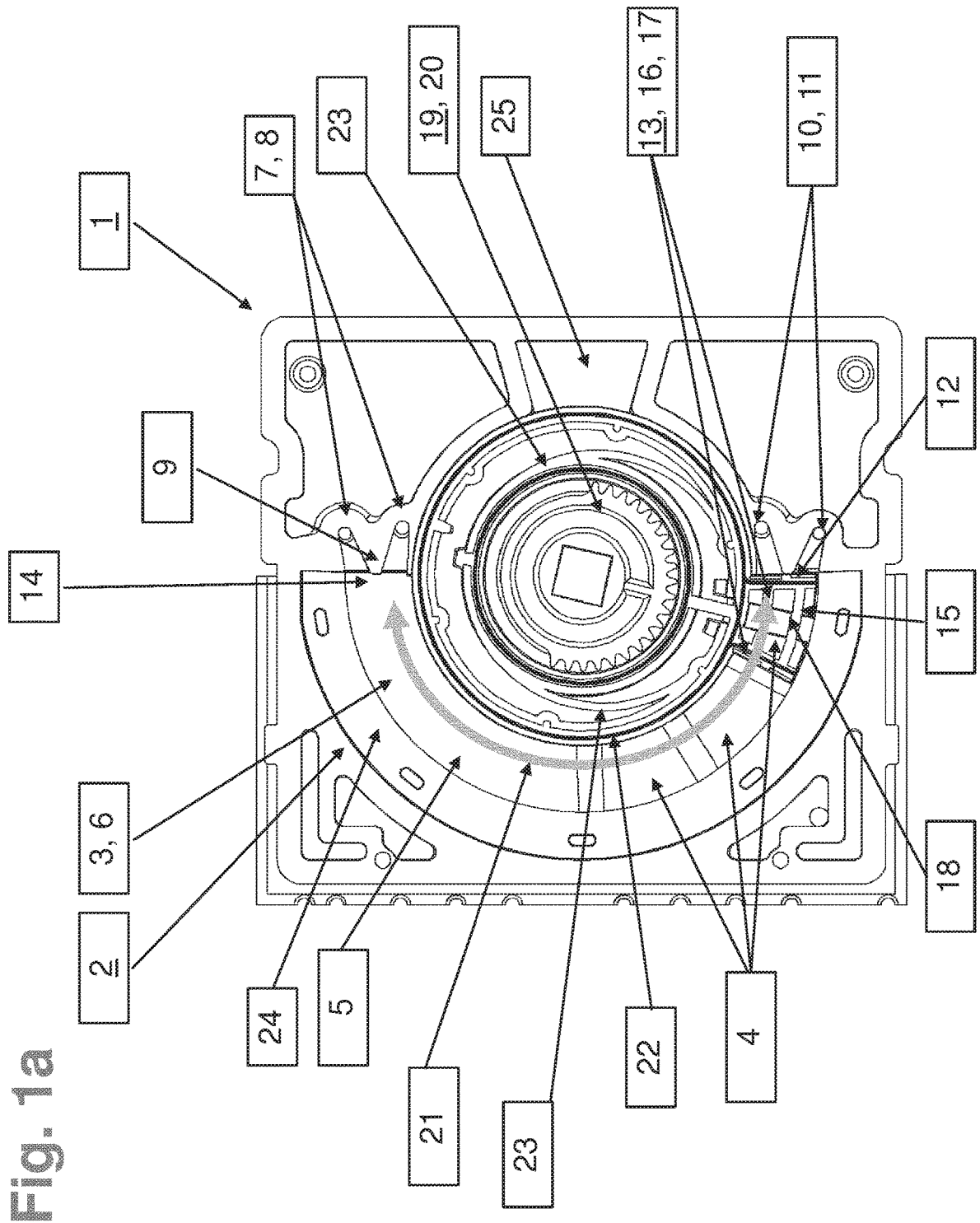
FIG. 1a shows an exemplary embodiment of an individual component of a device according to the invention comprising a rotatable adjusting means and a curved chamber design, wherein the separating element in a position at a lower terminal point.
Figure 1B:
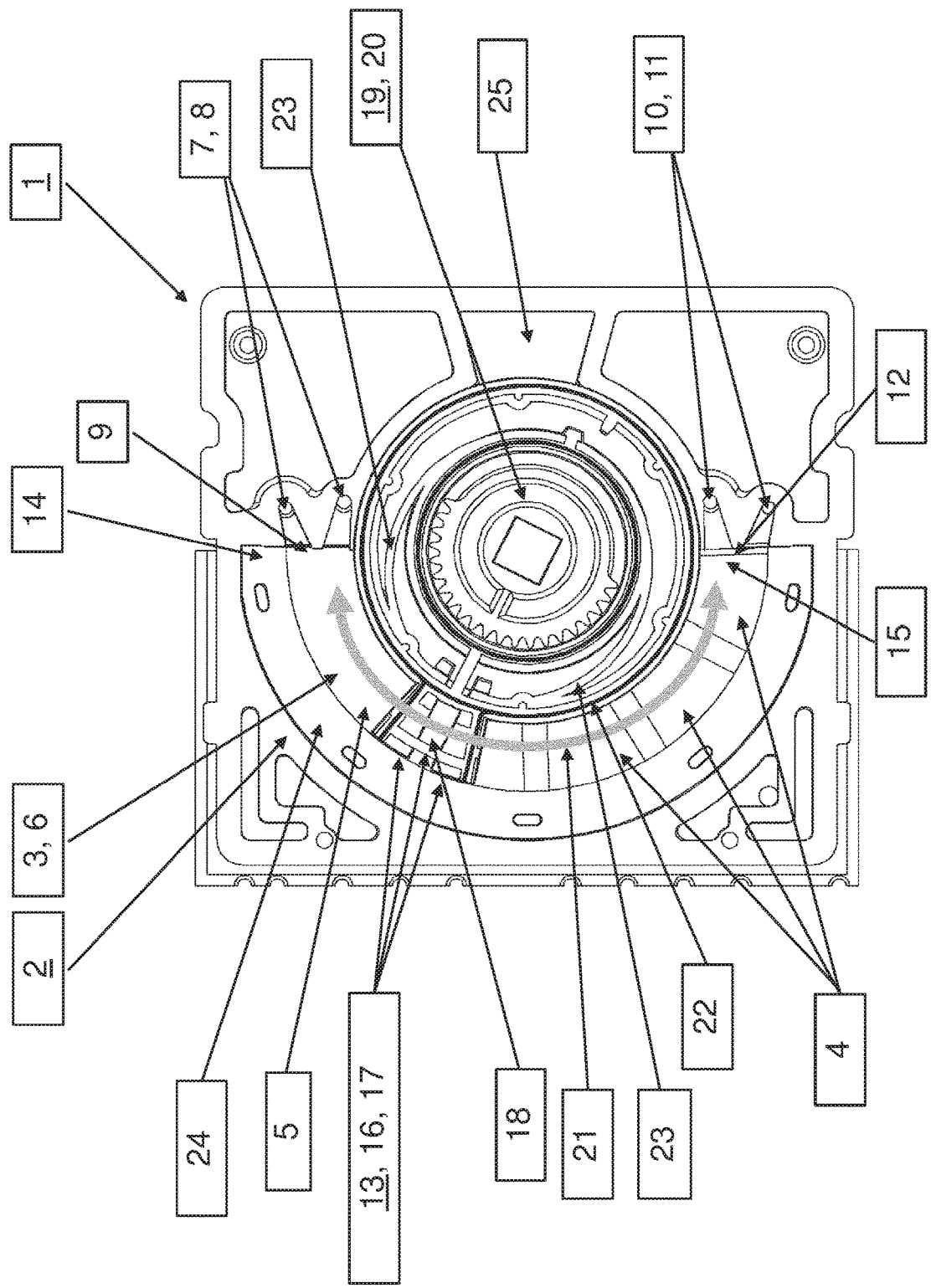
FIG. 1b corresponds to FIG. 1a, but shows the separating element in an intermediate position.

FIGS. 1a and 1b show an exemplary embodiment of an individual component of a device 1 according to the invention. The device 1 comprises a base member 2 having a curved recess 3 which is provided with four electrodes 4, 5. Three of these electrodes are segment electrodes 4 while one electrode is a counter electrode 5. The base member 2 represents one component of the device 1 which is assembled of two components that are attached to each other, wherein at least the inner sides of these components are identical. That is, the base member 2 and a second base member (base member 30 shown in FIG. 3) having an identical inner side are attached to each other so that the recess 3 and a corresponding recess of the second base member form a chamber 6 for holding a suspension of cells, cell derivatives, organelles, sub-cellular particles and/or vesicles. In this chamber 6 an electric field can be applied to the cells, cell derivatives, organelles, sub-cellular particles and/or vesicles, e.g., for transferring biologically active molecules such as nucleic acids or proteins into the cells, cell derivatives, organelles, sub-cellular particles and/or vesicles. To this end, the electrodes 4, 5 of base member 2 and the corresponding electrodes of the second base member establish electrode pairs, wherein the segment electrodes 4 of base member 2 and an oppositely arranged counter electrode of the second base member establish three electrode pairs while the counter electrode 5 of base member 2 and three oppositely arranged segment electrodes of the second base member also establish three electrode pairs. In this configuration the counter electrode 5 of base member 2 and the counter electrode of the second base member are each common electrodes of three segments so that the chamber 6 comprises six segments, wherein each segment is provided with one segment electrode and an area of one common counter electrode.

Two ports 7, 8 are disposed at one end 9 of the chamber 6 and two ports 10, 11 are disposed at the opposite end 12 of the chamber 6. One port of the upper ports 7, 8 can be used as inlet port for charging the chamber 6 and the other port of ports 7, 8 can be used as outlet port for discharging the chamber 6. Similarly, one port of the lower ports 10, 11 can be used as inlet port for charging the chamber 6 and the other port of ports 10, 11 can be used as outlet port for discharging the chamber 6. Accordingly, each end 9, 12 is provided with two ports 7, 8, 10, 11 through which the respective compartment of the chamber 6 can be filled with the suspension and/or through which the suspension can be purged out of this compartment. This configuration allows for simultaneous charging and discharging of the chamber 6 so that the time necessary for changing the suspension and hence the time lag between two subsequent electrical treatments of the suspension is minimized. Provision of the ports 7, 8, 10, 11 at opposite ends 9, 12 of the chamber 6 allows for easily establishing a push-pull mechanism where the suspension can be moved between the two ends 9, 12 of the chamber 6 so as to simultaneously charge one compartment at one end 9 of the chamber 6 and discharge another compartment at the opposite end 12 of the chamber 6. Accordingly, the device 1 is not a flow-through device but a device that enables charging and discharging of the chamber 6 at the same time by a push-pull mechanism wherein the liquid always leaves the chamber on the same side as it entered it.

Figure 2A:
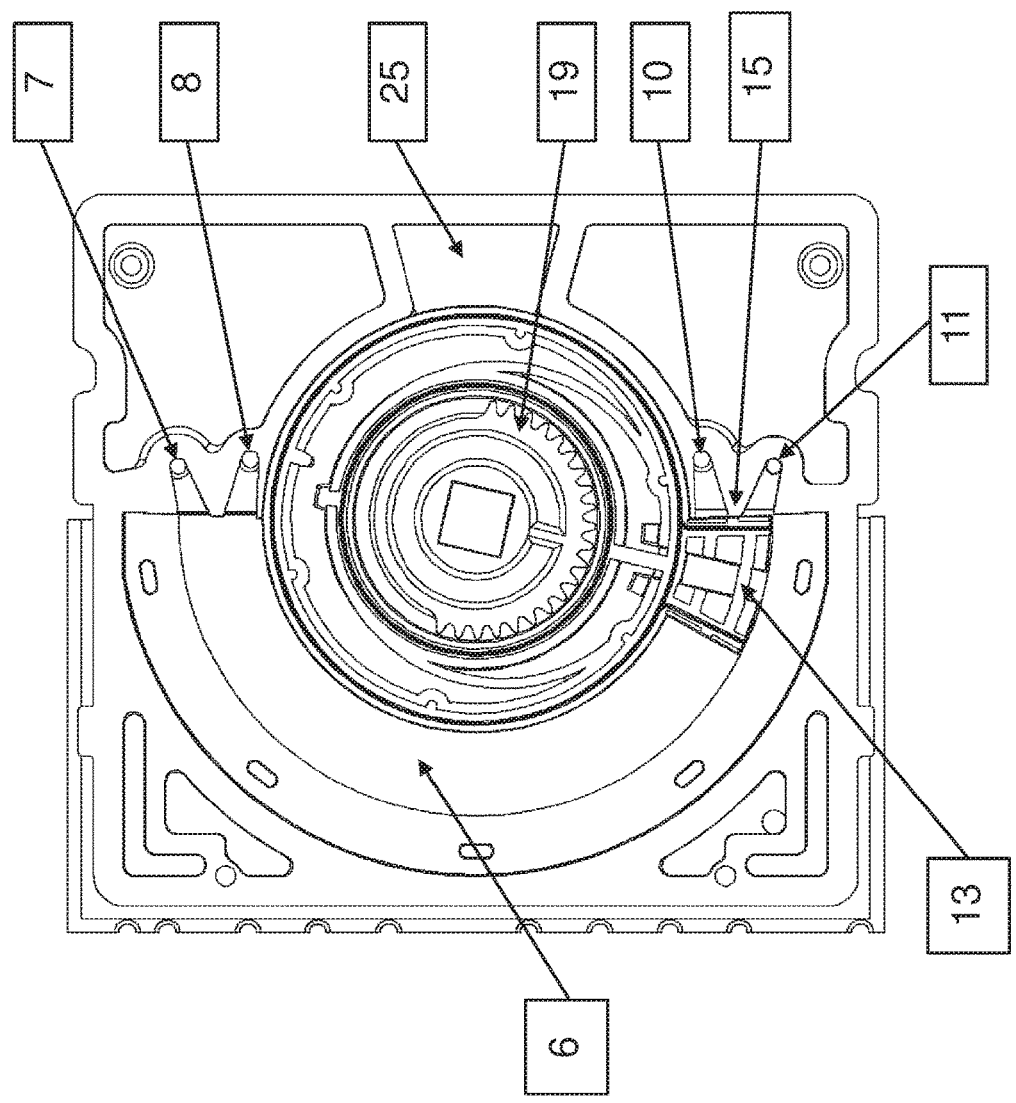
FIGS. 2a, 2b, 2c and 2d shows a schematic representation of different positions of the separating element of the device according to FIG. 1. The position in FIG. 2a is at a lower terminal point, the position in FIG. 2b is at an upper terminal point, the position in FIG. 2c is an Intermediate position and the position in FIG. 2d is a parking position.
Figure 2B:
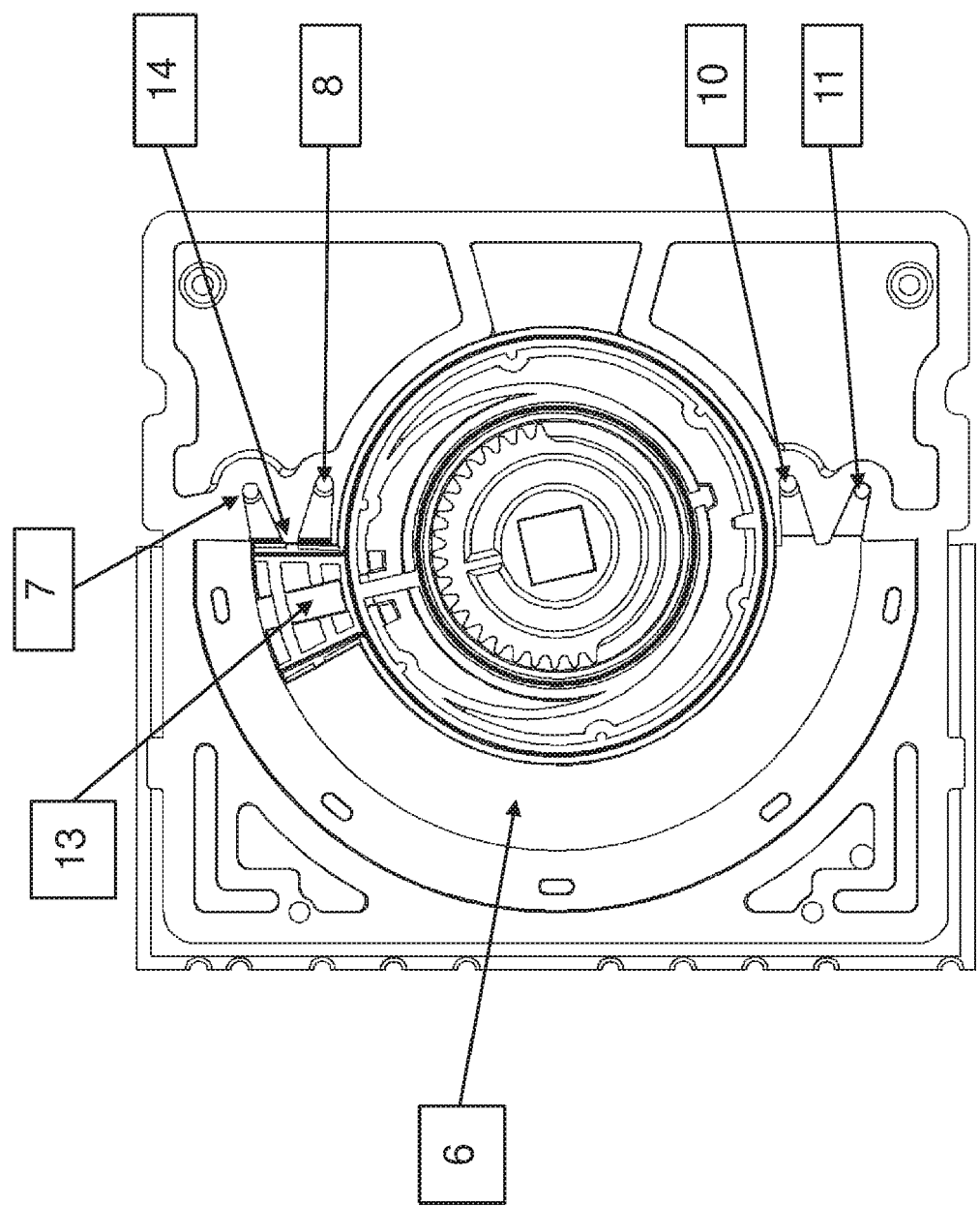
Figure 2C:
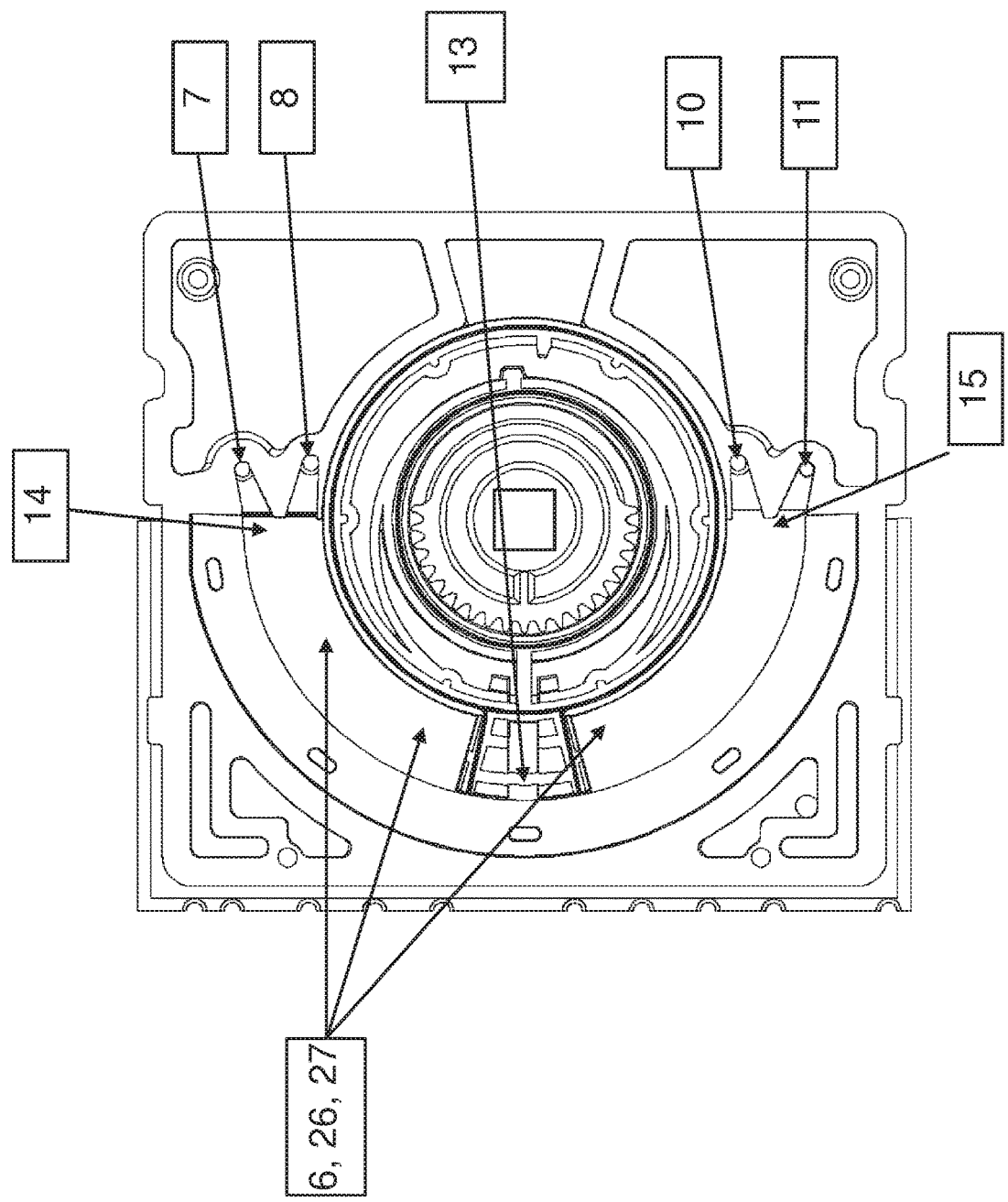

In order to separate the suspension that has already been treated by the electric field from the suspension to be treated, a separating element 13 is provided. The separating element 13 can be moved within the chamber 6 between two terminal points 14, 15 and divides the chamber 6 into two compartments if it is in a position between the two terminal points 14, 15 as depicted in FIGS. 1b and 2c. In the exemplary embodiment depicted in FIGS. 1 and 2 the separating element 13 comprises two parts 16, 17 which are spaced from each other and flank an inner space 18 comprising a compressible material. The two spaced parts 16, 17 are wiper-like fingers so that the separating element 13 is a sealing member which ensures liquidproof and/or gasproof separation of the different compartments of the chamber 6 if it is in a position between the terminal points 14, 15 (FIGS. 1b and 2c). To this end, the separating element 13 can be made of a flexible and/or elastic material so that is also capable of compensating pressure peaks within the chamber 6. The separating element 13 may further comprise sealing lips for optimal clearing of the chamber 6. The compressible material that fills the inner space 18 may be air or any other gas, or a compressible foam or cellular material, so as to provide effective pressure compensation in the chamber 6. Accordingly, the separating element 13 also acts as a kind of cushion that balances pressure variations in the chamber 6.

The separating element 13 is coupled to an adjusting element 19 which operates and/or controls the separating element 13. That is, the separating element 13 can be moved within the chamber 6 by means of the adjusting element 19. The adjusting element 19 is disposed outside the chamber 6 so that each compartment of the chamber 6 is devoid of any interfering element that might affect the function of the device 1. The adjusting element 19 comprises a rotatable body 20 which is operatively coupled with the spaced parts 16, 17 of the separating element 13. In this exemplary embodiment the rotatable body 20 is a rotor-like element that moves the separating element 13 such that it can perform a rotational movement along the double arrow 21. This embodiment ensures precise control and constant movement of the separating element 13 within the curved chamber 6. The rotatable body 20 is surrounded by a gasket 22 sealing the adjusting element 19 against the chamber 6, wherein the rotatable body 20 is connected to the gasket 22 via spokes 23 made of an elastic material.

The device 1 further comprises a sealing inlay 24 which extends along the outer side of the chamber 6 opposite to the gasket 22 described above and seals the compartments 26 and 27 of the chamber 6 against each other. The sealing inlay 24 is made of an elastic and compressible material, e.g., silicone foam or a similar inert material, so that it enables pressure compensation within the chamber.

Figure 2D:
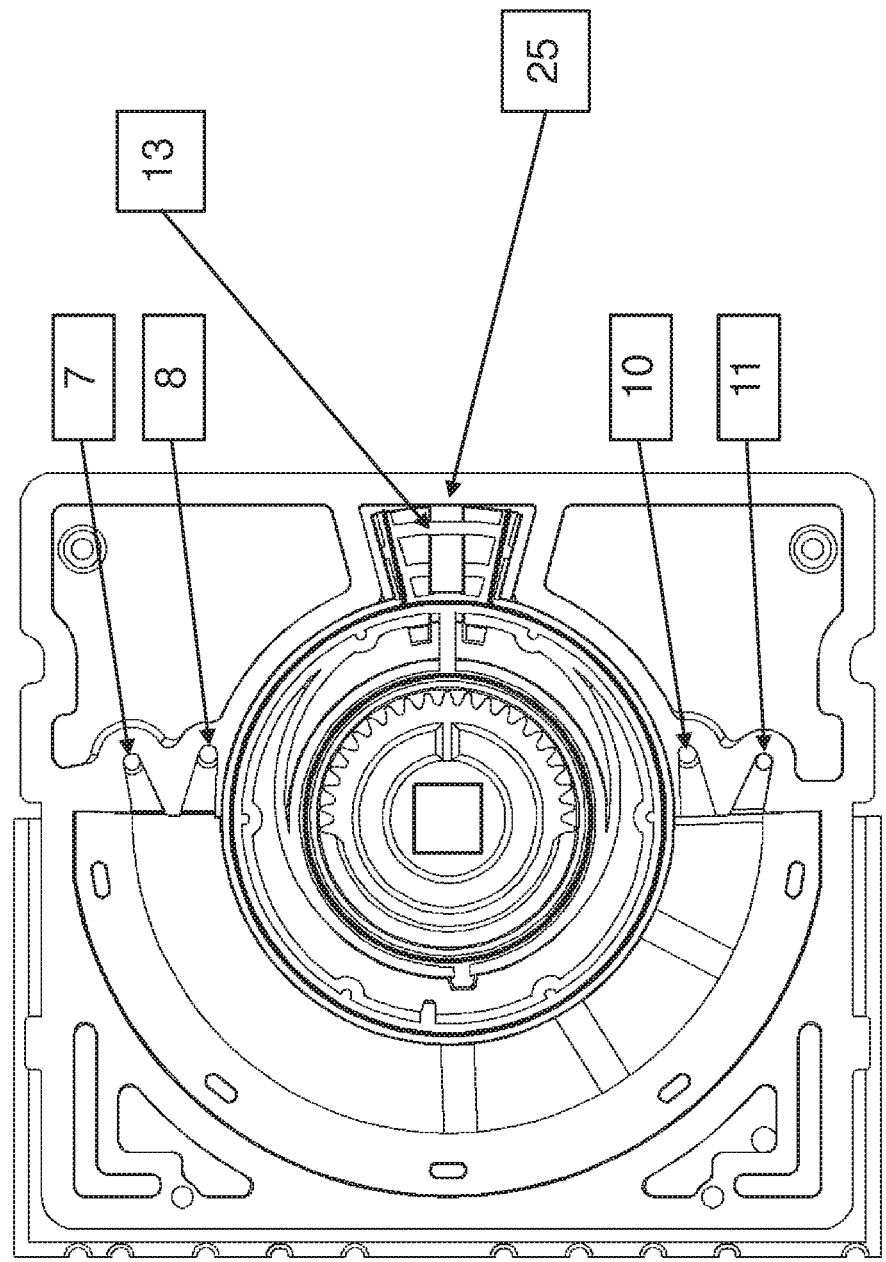

Advantageously, the device 1 includes means for fixing the separating element 13 outside the chamber 6, so that the scalable chamber 6 can be easily transformed into a static chamber 6 having a fixed volume as shown in FIG. 2d. To this end, the separating element 13 is moved by means of the adjusting element 19 to a parking site 25 where it is fixed, so as to provide the entire volume of the chamber 6 for processing of the suspension in a batch process. FIGS. 2a-d show different positions of the separating element (13) of the device 1 according to FIG. 1. The method according to the invention is a scalable process for electrically treating a suspension of cells, cell derivatives, organelles, sub-cellular particles and/or vesicles. In FIG. 2a) the separating element 13 is set to a position at the lower terminal point 15. If the separating element 13 is rotated to a position at the upper terminal point 14 (FIG. 2b)), a first aliquot of the suspension is injected into one of the lower ports 10, 11 and thus charged into the chamber 6. The first aliquot is then processed in the chamber 6 by applying an electric field to the suspended cells, cell derivatives, organelles, sub-cellular particles and/or vesicles. Subsequently, the processed first aliquot is discharged through one of the lower ports 10, 11 by rotating the separating element 13 back to the position at the lower terminal point 15 and, at the same time, a second aliquot of the suspension is injected into one of the upper ports 7, 8 and thus charged into the chamber 6. The second aliquot is then processed in the chamber 6 by applying an electric field to the suspended cells, cell derivatives, organelles, sub-cellular particles and/or vesicles. Subsequently, the processed second aliquot is discharged through one of the upper ports 7, 8 by rotating the separating element 13 back to the position at the upper terminal point 14 and, at the same time, a third aliquot of the suspension is injected into one of the lower ports 10, 11 and thus charged into the chamber 6. The third aliquot is then processed in the chamber 6 by applying an electric field to the suspended cells, cell derivatives, organelles, sub-cellular particles and/ or vesicles. This push-pull mechanism with simultaneous charging and discharging of the suspension can be repeated until the whole suspension is treated.

The separating element 13 separates the chamber 6 in two compartments 26, 27 if it is in a position between the terminal points 14, 15 (FIG. 2c)), wherein each compartment 26, 27 of the chamber 6 is designed to hold a suspension and comprises two ports 7, 8 and 10, 11 for charging or discharging the chamber 6. Each compartment 26, 27 can receive and hold an aliquot of the suspension which is movable in and out of the chamber 6 through at the ports 7, 8 and 10, 11. The compartments 26, 27 are each further provided with one port 7, 10 through which the respective compartment 26, 27 can be filled with the suspension and with one port 8, 11 through which the suspension can be purged out of this compartment 26, 27. When the separating element 13 is rotated, one compartment 26, 27 of the chamber 6 is filled with an aliquot of the sample, while another aliquot of the sample is discharged and pushed out from the other compartment 26, 27. A container for incoming sample can be connected to an upper and a lower inlet port 7, 10 and an upper and a lower outlet port 8, 11 can be connected to a reservoir for processed sample. As becomes apparent from FIG. 2, the device 1 does not work in flow through-fashion but in a push-pull manner wherein injected sample is discharged after processing on the same side where it was charged. The chamber 6 possesses six electrode segments, one of which being always covered by the separating element 13 and thus is not usable. For example, the chamber 6 can take 1000 µl per cycle. Thus, in this case, 2000 µl can be processed in a complete cycle.

In an advantageous embodiment of the invention the separating element is adjusted such that it covers exactly one or more segment electrodes so that the same electrical parameters can be established within each other electrode segment.

The static variant of the device 1 does not allow the separating element 13 to rotate. Instead the separating element 13 is fixed outside the chamber 6 at the parking site 25, not covering any electrode segment as shown in FIG. 2d. With this variant all six electrode segments can be used and thus 1200 µl sample can be processed. For example, the sample can be injected at a lower or upper inlet port 7, 10 of the device 1 and can be collected at the lower outlet port 11. Repetitive filling is not possible in this state of the device 1.

Figure 3:
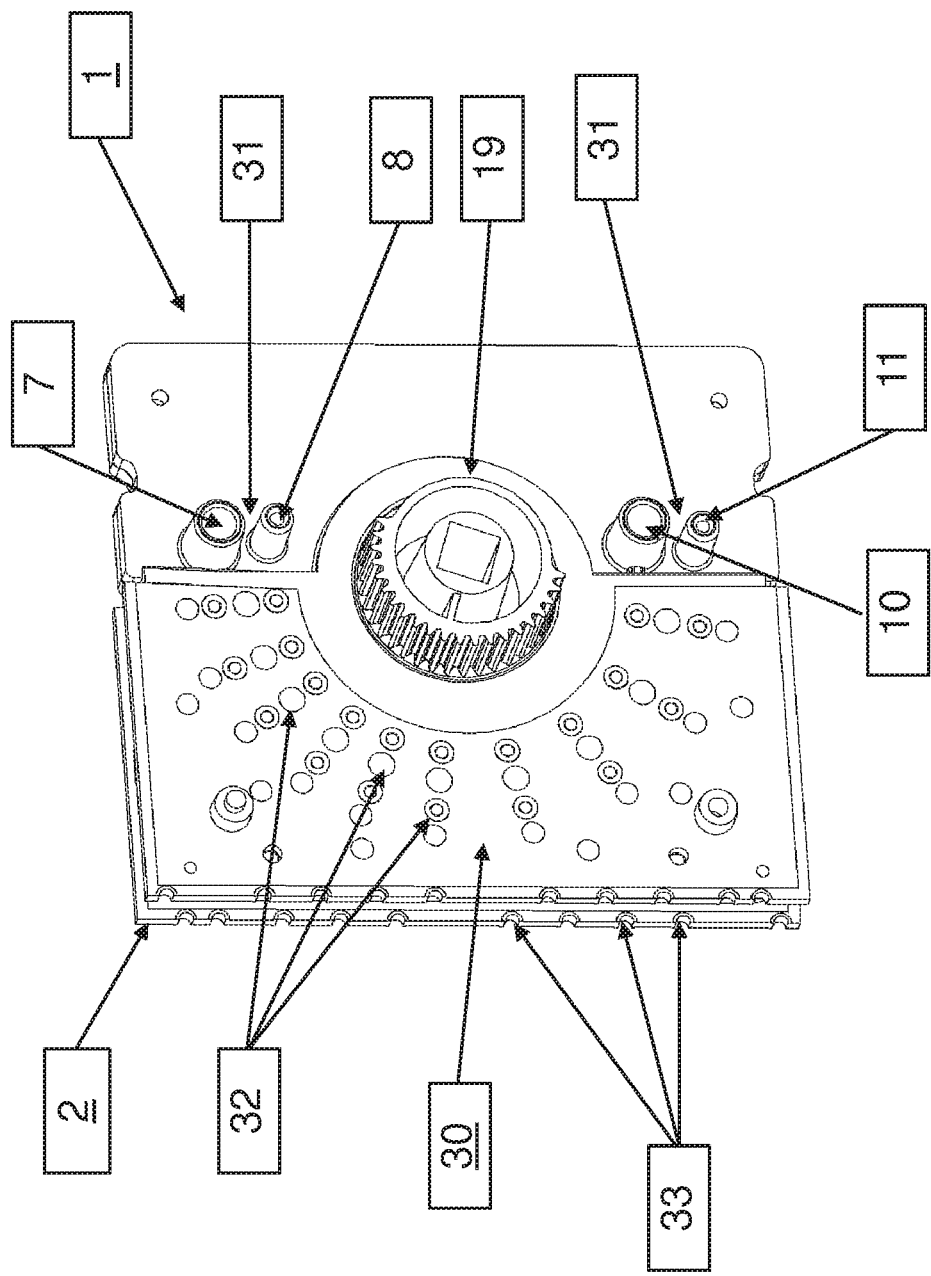
FIG. 3 shows a perspective view of the outer side of the device according to FIG. 1.

FIG. 3 shows a perspective view of the outer side of the device 1 according to FIG. 1. The device 1 comprises a base member 30, the inner side of which (not visible) being identical to the inner side of the base member 2 according to FIG. 1. The base member 30 represents a further component of the device 1 which is assembled of two components (base members 2 and 30) that are attached to each other. At its outer side, the base member 30 is provided with connectors 31 for connecting conduits to the ports 7, 8, 10, 11 of the chamber 6 according to FIGS. 1 and 2. One or more containers for the suspension to be processed and one or more reservoirs for processed suspension can be connected to the connectors 31 via suitable conduits. The suspension can be charged into and discharged from the chamber by means of a pumping element, e.g., a vacuum pump or a peristaltic pump or the like, which may be connected to the suspension circuit between the container(s)/reservoir(s) and the connectors 31. In order to render the device 1 compatible with common conduits and pumping systems, the connectors 31 can be Luer slip or Luer lock connectors.

The adjusting element 19 of the device 1 may be connected to a power unit (not shown), e.g., an electric motor, via a worm gear, a spur gear, a bevel gear, a gear rod, a belt drive, a square-bar steel, or similar gear mechanisms or power transmission elements (not shown).

The base member 30 further comprises a multitude of conductive areas 32 for providing electric connection to the electrodes in the chamber. The conductive areas 32 may comprise an electrically conductive polymer, in particular a polymer doped with electrically conductive material or an intrinsically conductive polymer. The conductive areas 32 are designed to provide an electrical connection between the electrodes and at least one electric contact point 33. In this embodiment the conductive areas 32 are holes in the base member 30 which are at least partially filled with the electrically conductive material. The conductive areas 32 are electrically coupled with at least one electric contact point 33 via at least one conductive path (not shown). The electric contact point can be contacted by at least one electric contact, so as to provide direct or indirect electric connection to a power source.

FIGS. 4a and 4b show different views of the base member 30 according to FIG. 3. The inner surface 34 of the base member 30 is depicted in FIG. 4a). Electrodes 4, 5 are attached to the inner surface 34. Three of these electrodes 4, 5 are segment electrodes 4 while one of these electrodes 4, 5 is a larger counter electrode 5. The electrodes 4, 5 are attached and connected to conductive areas 32 which extend from the inner surface 34 to the outer surface 35 of the base member 30. For example, the electrodes 4, 5 and the electrically conductive material within the conductive area 32 are made of the same material, e.g., an electrically conductive polymer, in particular a polymer doped with electrically conductive material or an intrinsically conductive polymer as described above. The polymer can be molded over the inner surface 34 and the conductive area 32 of the base member 30 and extend through holes of the conductive area 32 as shown in detail in FIG. 5a). The conductive areas 32 are electrically coupled with at least one electric contact point 33 via at least one conductive path (not shown). The electric contact point 33 can be contacted by at least one electric contact, so as to provide direct or indirect electric connection to a power source. In an advantageous embodiment of the invention the base member 30 is a Printed Circuit Board (PCB).

Figure 5C:
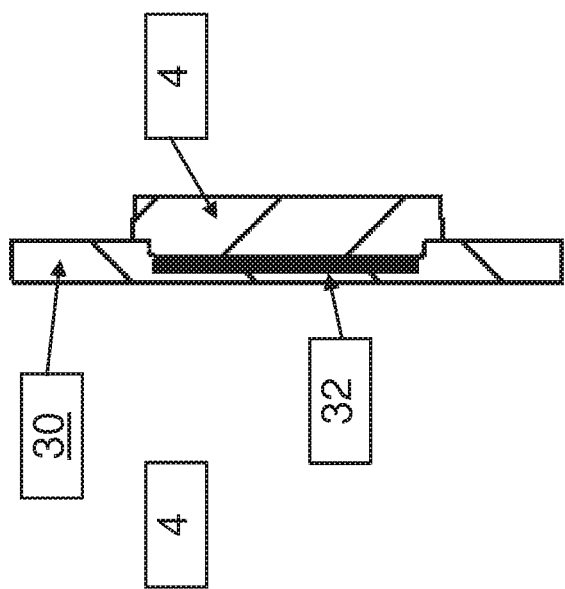
FIGS. 5a, 5b and 5c show details of three exemplary embodiments of the device according to FIGS. 3 and 4. In particular.
Figure 5B:
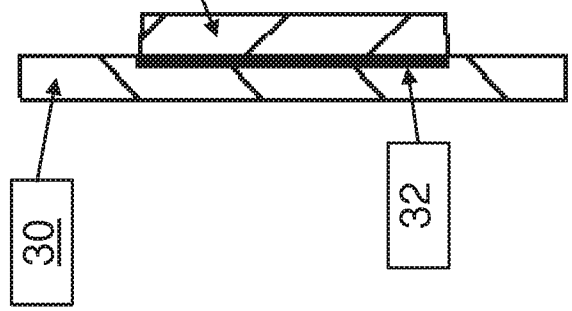
Figure 5A:
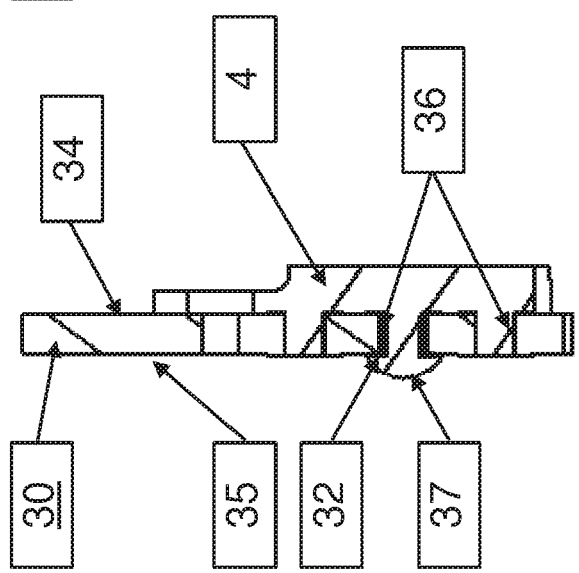

FIGS. 5a-c show details of three alternative embodiments of the device according to FIGS. 3 and 4. As described with reference to FIGS. 3 and 4, the base member 30 includes conductive areas 32 to which electrodes 4 are attached. In the embodiment shown in FIG. 5a), which is also realized in the device shown in FIGS. 3 and 4, the conductive area 32 comprises holes 36 that are at least partially filled with an electrically conductive material. If the conductive material protrudes a hole 36 and forms a kind of bulge 37 at the outer surface 35 of the base member 30, stability of the connection of the electrode 4 to the base member 30 is increased in an advantageous manner. In the embodiments shown in FIGS. 5b) and 5c), the conductive areas 32 do not comprise holes that are filled with a conductive material but either a flat surface (FIG. 5b)) or a recess (FIG. 5c)) comprising an electrically conductive material. Thus, the electrodes 4 can alternatively be either attached to a flat surface or a recess of the base member 30.

What we claim is:

1. Device for applying an electric field to a suspension of cells, cell derivatives, organelles, sub-cellular particles and/or vesicles, comprising:
   at least one chamber which comprises
   at least two segments, each segment comprising a first electrode and a second electrode,
   wherein the first electrode is one segment electrode of a segmented electrode comprising at least two segment electrodes and
   the second electrode is a single unsegmented electrode concurrently common to the at least two segments,
   wherein each segment is electrically addressable individually, and
   wherein the chamber further comprises corresponding recesses of two components which are attached to each other, the aligned recesses forming the chamber, wherein each recess is provided with the first and the second electrode.

2. The device according to claim 1, wherein the first electrode and the second electrode form an electrode pair providing an electric field.

3. The device according to claim 1, wherein the chamber further comprises at least one base member which is substantially made of an insulating material and includes at least one surface to which the first and/or second electrode is attached, wherein said surface comprises at least one conductive area designed to provide an electrical connection between the first and/or second electrode and at least one electric contact point.

4. The device according to claim 3, wherein the conductive area is a pit or hole being at least partially overmolded or filled with an electrically conductive material and providing an electrically conductive path from the first and/or second electrode to the contact point.

5. The device according to claim 4, wherein the first and/or second electrode and the electrically conductive material are made of the same material.

6. The device according to claim 3, wherein the base member is a Printed Circuit Board (PCB).

7. The device according to claim 1, wherein the chamber comprises at least one sealing inlay which at least partially extends along one side of the chamber, wherein the sealing inlay comprises a compressible material.

8. The device according to claim 1, wherein the two components are identical and the identical components are rotationally symmetric.

9. The device according to claim 1, further comprising at least one separating element which is movable within the chamber between two terminal points.

10. The device according to claim 9, wherein the separating element is fixed outside the chamber.

11. The device according to claim 10, wherein the separating element is fixed at a parking site.

12. The device according to claim 3, wherein the first and second electrode are attached to the at least one surface of the at least one base member.

13. The device according to claim 12, wherein the at least one conductive area is designed to provide an electrical connection between, both, the first and the second electrode and at least one electric contact point.

* * * * *